United States Patent
Weatherhead et al.

(10) Patent No.: US 10,391,243 B2
(45) Date of Patent: Aug. 27, 2019

(54) DETECTING DEPTH OF ANESTHESIA VIA PUPIL METRICS

(71) Applicant: EYETRACKING LLC

(72) Inventors: James J. Weatherhead, San Diego, CA (US); Sandra Marshall, San Diego, CA (US)

(73) Assignee: EYETRACKING LLC, Solana Beach, CA (US)

( * ) Notice: Subject to any disclaimer, the term of this patent is extended or adjusted under 35 U.S.C. 154(b) by 1171 days.

(21) Appl. No.: 14/322,889

(22) Filed: Jul. 2, 2014

(65) Prior Publication Data

US 2015/0011968 A1    Jan. 8, 2015

Related U.S. Application Data (60) Provisional application No. 61/842,235, filed on Jul. 2, 2013.

(51) Int. Cl.
| | |
|---|---|
| *A61B 3/11* | (2006.01) |
| *A61B 5/00* | (2006.01) |
| *A61B 5/107* | (2006.01) |
| *A61M 5/172* | (2006.01) |
| *A61B 3/14* | (2006.01) |

(52) U.S. Cl.
CPC .......... *A61M 5/1723* (2013.01); *A61B 3/112* (2013.01); *A61B 5/1079* (2013.01); *A61B 5/4821* (2013.01); *A61M 2202/048* (2013.01); *A61M 2205/18* (2013.01); *A61M 2205/3303* (2013.01); *A61M 2205/52* (2013.01)

(58) Field of Classification Search
CPC ............ A61M 5/1723; A61M 2205/18; A61M 2205/3303; A61M 2205/52; A61B 3/112; A61B 2202/048; A61B 5/1079; A61B 5/4821
USPC .................................................. 351/206, 209
See application file for complete search history.

(56) References Cited

U.S. PATENT DOCUMENTS

| | | | | |
|---|---|---|---|---|
| 2010/0269820 | A1* | 10/2010 | Danielsen ............. | A61M 16/18 128/202.22 |
| 2011/0170064 | A1* | 7/2011 | Taylor .................. | A61B 3/0083 351/209 |
| 2011/0295196 | A1* | 12/2011 | Chazot ................ | A61M 5/1723 604/66 |

(Continued)

OTHER PUBLICATIONS

Francesco Inchingolo, Marco Tatullo, Fabio M. Abenavoli, Massimo Marrelli, Alessio D. Inchingolo, Bruno Villabruna, Angelo M. Inchingolo, Gianna Dipalma. Severe Anisocoria after Oral Surgery under General Anesthesia. International Journal of Medical Sciences 2010; 7(5):314-318 (Year: 2010).*

*Primary Examiner* — Collin X Beatty
(74) *Attorney, Agent, or Firm* — Edward D. Grieff; Mintz, Levin, Cohn, Ferris, Glovsky and Popeo, P.C.

(57) ABSTRACT

A video feed of one or more pupils of a patient can be received and processed to determine a raw measure of pupil size of the one or more pupils over time. Based on this raw measure, at least one of a) a depth of anesthesia for the patient, b) an index of cognitive activity for the patient, and c) a degree of perfusion of an anesthetic being administered to the patient to one or both hemispheres of a brain of the patient can be determined such that one or more actions can be caused to be performed. Related systems, methods, and article of manufacture are described.

22 Claims, 4 Drawing Sheets

Fig. 4

(56) References Cited

U.S. PATENT DOCUMENTS

| | | | |
|---|---|---|---|
| 2014/0185010 A1* | 7/2014 | Bernert | A61B 3/112 351/219 |
| 2014/0268047 A1* | 9/2014 | Hirsh | A61B 3/112 351/206 |
| 2015/0038940 A1* | 2/2015 | Kreuer | A61M 5/1452 604/503 |
| 2015/0223682 A1* | 8/2015 | Kamkar | A61B 3/112 351/206 |

* cited by examiner

DETECTING DEPTH OF ANESTHESIA VIA PUPIL METRICS

CROSS-REFERENCE TO RELATED APPLICATION

The current application claims priority under 35 U.S.C. § 119(e) to U.S. provisional application No. 61/842,235 filed Jul. 2, 2013, the disclosure of which is incorporated herein by reference.

TECHNICAL FIELD

The subject matter described herein relates to techniques, systems, and the like for analyzing a depth of anesthesia currently being experienced by a subject, such as for example a surgical or other medical patient.

BACKGROUND

During surgery, anesthesiologists administer one or more drugs, which can include but are not limited to Propofol and the like, to sedate or relax patients while undergoing surgical procedures. It is the anesthesiologist's responsibility to ensure that the correct level of drug is provided to the patient to ensure, among other things, that the patient is not too heavily sedated (which could lead to issues such as longer recovery times, or, in extreme cases, even death), or not sedated enough, which could lead to the patient waking up or not being fully unconscious and hence being aware of the surgical procedure, perhaps even feeling pain. Other things that would be of benefit to the anesthesiologist can include the ability to check for perfusion of the drug(s) across cerebral hemispheres to ensure that both sides of the brain are affected by the drug, as well as the ability to keep a patient "just unconscious" so they could quickly be awoken for checking responses etc. (the latter being common during neurology procedures as an example).

Under current practices, anesthesiologists generally use tools such as the Bispectral index (e.g. via a BIS monitor) in an attempt to measure depth of anesthesia. A BIS monitor tool uses electrode(s) attached to the patient's forehead and purportedly gives a useful measure of depth of anesthesia. However, a BIS monitor suffers from a number of drawbacks. One concern is that it does not rely on any underlying physiological model of brain function or generation of awareness. Another problem is that the BIS number is insensitive to several commonly used anesthetic agents and therefore it is questionable to what degree it indicates awareness. Additionally, the calculations performed by a BIS monitor are computer-intensive. In view of the questionable reliability and practicality of a BIS monitor, the medical community generally uses such tools as a guide rather than a definitive answer to anesthesia level. Anesthesiologists also use other measures in conjunction with BIS readings in an effort to gauge the patient's state. Such measures can include pupil size, heart rate, respiration, sounds from the patient, and others. However, the effectiveness of these measures relies on subjective assessment by the anesthesiologist and are therefore potentially subject to human error.

SUMMARY

In one aspect, a method includes receiving a video feed of one or more pupils of a patient from at least one video camera positioned to view the one or more pupils and processing the video feed to determine a raw measure of pupil size of the one or more pupils over time. Based on the raw measure of pupil size over time, at least one of a) a depth of anesthesia for the patient, b) an index of cognitive activity for the patient, and c) a degree of perfusion of an anesthetic being administered to the patient to one or both hemispheres of a brain of the patient is determined. Execution of one or more actions is caused based on the determining.

In some variations one or more of the following features can optionally be included in any feasible combination. The one or more actions can include any of commanding an anesthesia machine to change an administered amount of one or more drugs, triggering an alert indicating that a level of anesthesia for the patient is too high or low, triggering an alert indicating that the anesthetic being administered to the patient has not perfused correctly to both hemispheres of the brain, or the like. The processing can include sampling the video feed at approximately 1 Hz to 1000 Hz. The method can include at least one of averaging and smoothing the raw measure of pupil size to remove at least one of noise and data artifacts. The at least one video camera can include an infra-red light camera, and the receiving can include recording the video feed while an eyelid of the patient is closed. Alternatively or in addition, the at least one video camera can include a visible light camera, and the receiving can include recording the video feed while an eyelid of the patient is at least periodically opened. The patient can be conscious or unconscious during the receiving. The patient can be receiving at least one of an anesthetic and a pain-relief medication during the receiving.

Implementations of the current subject matter can include, but are not limited to, methods consistent with the descriptions provided herein as well as articles that comprise a tangibly embodied machine-readable medium operable to cause one or more machines (e.g., computers, etc.) to result in operations implementing one or more of the described features. Similarly, computer systems are also described that may include one or more processors and one or more memories coupled to the one or more processors. A memory, which can include a computer-readable storage medium, may include, encode, store, or the like one or more programs that cause one or more processors to perform one or more of the operations described herein. Computer implemented methods consistent with one or more implementations of the current subject matter can be implemented by one or more data processors residing in a single computing system or multiple computing systems. Such multiple computing systems can be connected and can exchange data and/or commands or other instructions or the like via one or more connections, including but not limited to a connection over a network (e.g. the Internet, a wireless wide area network, a local area network, a wide area network, a wired network, or the like), via a direct connection between one or more of the multiple computing systems, etc.

The details of one or more variations of the subject matter described herein are set forth in the foregoing descriptions and the accompanying drawings (which are incorporated in and constitute a part of this specification and which, together with the description, help explain some of the principles associated with the disclosed implementations). Other features and advantages of the subject matter described herein will be apparent from the description and drawings.

DESCRIPTION OF DRAWINGS

The accompanying drawings, which are incorporated in and constitute a part of this specification, show certain aspects of the subject matter disclosed herein and, together with the description, help explain some of the principles associated with the disclosed implementations. In the drawings.

When practical, similar reference numbers denote similar structures, features, or elements.

DETAILED DESCRIPTION

To address the aforementioned and potentially other issues with currently available solutions, methods, systems, articles of manufacture, and the like consistent with one or more implementations of the current subject matter can, among other possible advantages, provide approaches relating to measurements of depth of anesthesia. An eye tracker, or pupilometer can be used to measure the patient's size of pupil over time before, after, and during anesthesia. An eye tracker (which includes one or multiple video cameras) and a computational component such as a personal computer can be located such that a view of the patient's eye(s) can be seen by the one or more video cameras. The video feed of the person's pupils is processed to allow an ongoing measure of pupil size to be generated and fed to a Depth of Anesthesia Algorithm (DOAA) as discussed herein.

The video cameras used by the system can be natural light based such as is used by traditional home video cameras, or infra-red (or 'near-infra red' light based) so that they can in some examples "see" through the patient's eyelids, allowing a measure to be recorded while the patient's eyes are closed. Combinations of one or more such approaches are within the scope of the current subject matter as well.

A system, method, etc. implementing the DOAA algorithm in conjunction with measurements of pupil characteristics can monitor one or both pupils (when both are visible to the camera or cameras) while the patient is awake. When the patient is unconscious, the anesthesiologist may need to periodically open the patient's eye or eyes in order for the system to be able to measure the pupil.

The DOAA implemented on a computing device can receive pupil readings at the rate that the connected eye tracker feeds to it. In some examples, an eye tracker can record data at 30 Hz to 1000 Hz, however this rate is not important for the DOAA to function. Typically the minimum sampling rate of pupil size would be one sample per second, and the maximum would be 1000 Hz, but it could exceed this range on either side. More samples allow for more data points, and hence a more stable reading (bad samples can be eliminated, or averaged out if needed).

Typically, it is observed that a person's pupils dilate as anesthetic is administered, and that the dilation is usually greater as the amount of anesthetic increases. As a visual confirmation of the depth of anesthesia which a patient is under, an anesthesiologist will typically look at a patient's pupil to confirm size as well as to ensure that both pupils are dilated uniformly. Noticeable differences in the amount of dilation between pupils may suggest that the anesthetic has not perfused correctly to both hemispheres of the brain, that the subject may not be fully unconscious, and may have at least some level of awareness.

Approaches consistent with implementations of the current subject matter can employ one or more measures and principles. Two such approaches, which are each independent of the other and which can be used individually or in combination, make use of pupil measure.

The first such measure uses the reported raw pupil size to determine depth of anesthesia. As the anesthetic is administered, the pupil size generally shrinks as the drug is perfused into the patient's body. While the exact size change will be different for each person, it has been seen that the pupil size will often shrink by approximately 20-30% from fully conscious to fully anesthetized. The change happens fairly quickly after the drug is administered (typically less than 60 seconds), although the timing of this change can be somewhat dependent on the body size and other physiology of the patient. As the drug is turned off and dissipates from the patient, the pupil size again increases as the patient's level of consciousness also increases. Consistent with some implementations of the current subject matter, the raw pupil data can be averaged or smoothed to remove noise or data artifacts.

The second measure relies on a pupil processing technique referred to as the "index of cognitive activity" (ICA). The ICA monitors brain activity though changes in pupil size and can be used to determine how conscious or unconscious a person is based on their cognitive function. As an example, a person experiencing pain, but not conscious enough to react to it, may show higher ICA readings.

While a tool or method consistent with implementations of the current subject matter can be used to measure depth of anesthesia, the current subject matter can also be used in other instances such as when a person is fully awake but is receiving pain medication though a delivery mechanism such as an epidural injection. The pupils of a conscious patient can be monitored to ensure that the drug has perfused to both hemispheres of the brain (by ensuring similarities in pupil size and behavior from both eyes), and also may reflect the amount of drug that has perfused by monitoring change in pupil size and/or behavior.

The approaches described herein are not limited to people; the patient could be a person or an animal.

Potential uses of the current subject matter can include performing one or more actions based on the determined depth of anesthesia for the patient and/or the determined index of cognitive activity for the patient and/or the degree of perfusion of the anesthetic to both brain hemispheres. The one or more actions can include triggering an alert or an alarm to one or more responsible persons (e.g. the anesthesiologist, another surgical team member, etc.) if the level of anesthesia is too high or low. Alternatively or in addition, the one or more actions can include automatically administering more or less anesthetic (or other drugs) based on the reported level of anesthesia, for example by sending a command to an anesthesia machine. The DOAA can have predefined levels or thresholds that can be set by the operator to trigger these events if any pre-defined thresholds in the system were not appropriate for a specific use.

Figure 1:
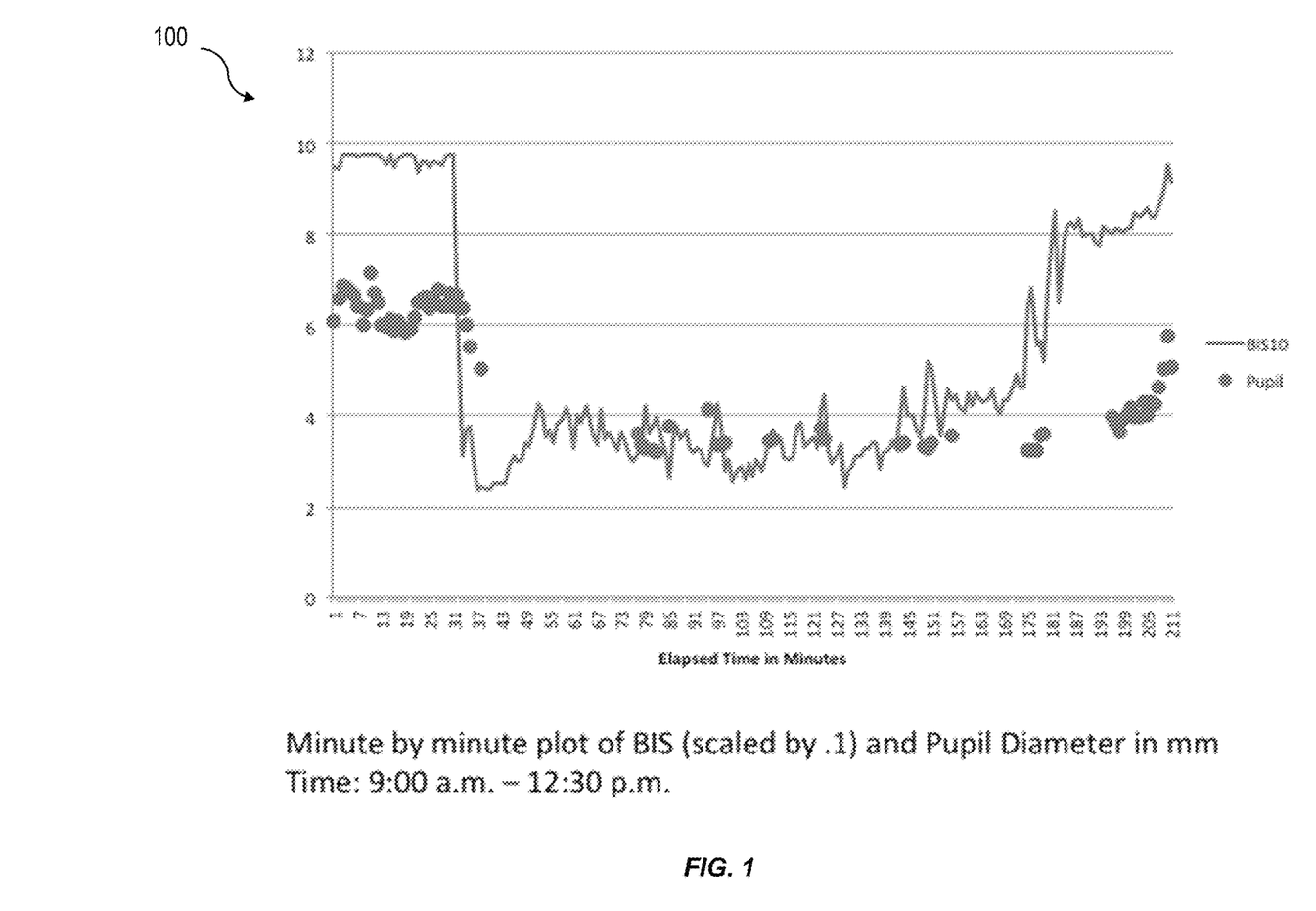
FIG. 1 shows a chart of minute-by-minute data for bispectral index data (scaled by 0.1) and pupil diameter.
Figure 2:
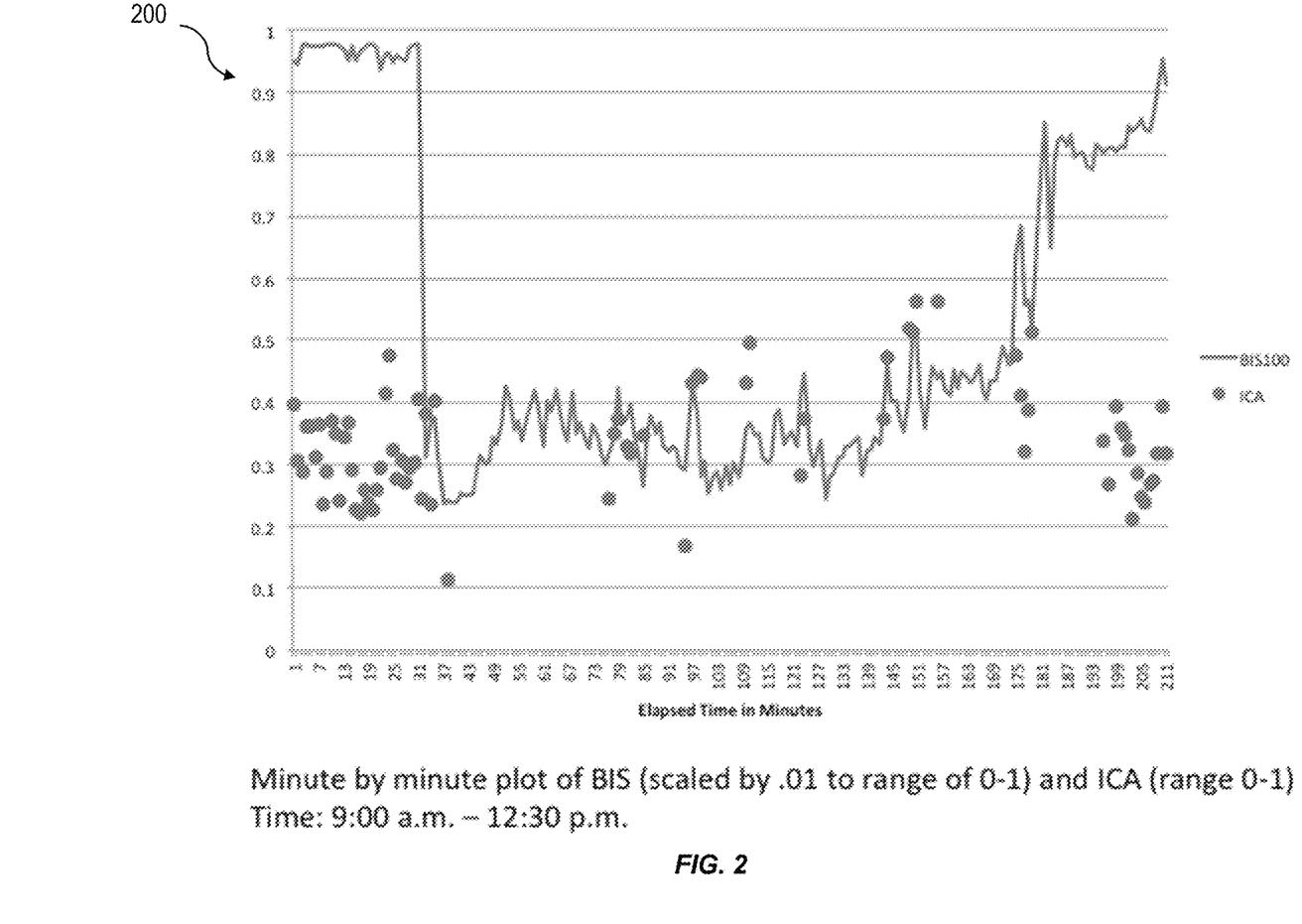
FIG. 2 shows a chart of minute-by-minute data for bispectral index BIS data (scaled by 0.1) and an index of cognitive activity.

FIG. 1 and FIG. 2 show, respectively, a chart 100 of minute-by-minute data for BIS data (scaled by 0.1) and pupil diameter in millimeters and a chart 200 of minute-by-minute data for BIS data (scaled by 0.01) and ICA. The methodology used to collect the data was as follows. Pupil measurements data were all data recorded from a patient's right eye. The BIS data was recorded automatically throughout the experimental trial as standard surgical procedure. The pupil data was not recorded continuously once the anesthetic was administered. At preset intervals, the subject's right eye was held open by a member of the anesthesiology team and data were recorded for 5-30 seconds. The pupil diameter was sampled at 60 Hz. Irregularities in the data (e.g., blinks, lost data, eyetracker spikes) were removed, and minute-by-minute averages were plotted. Index of Cognitive Activity (ICA) measurements were calculated from the pupil diameter data and were based on signal processing (i.e., wavelet analysis). This data was scaled to a range of 0-1, with 0 being low cognitive effort. Values were computed by the second and then averaged by minute. Despite the sparsity of pupil data as compared with the BIS data, they capture the main results shown in the BIS data. Both raw pupil diameter and the ICA show large changes following infusion of the anesthetic, as does the BIS monitor. And both pupil-based measures show gradual increases when the anesthetic infusion is stopped, as does the BIS monitor. However, the pupil metrics suggest that the BIS monitor reports a recovery from anesthetic that is more rapid than the brain activity that is measured through the pupil. The ICA also shows a higher level of activity during the later stages of anesthesia than does BIS monitor.

Figure 3:
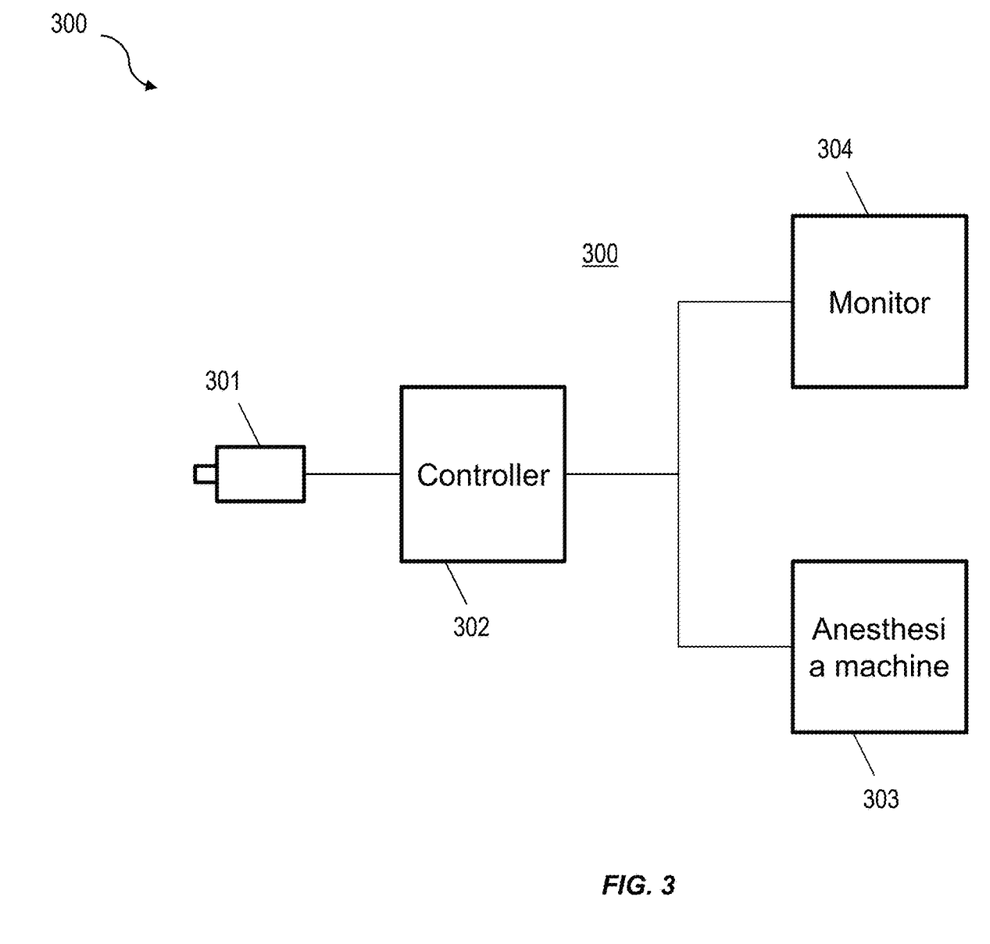
FIG. 3 shows a diagram illustrating aspects of a system showing features consistent with implementations of the current subject matter.

FIG. 3 shows a diagram 300 illustrating features of a system consistent with implementations of the current subject matter. In the system, a camera 301, which may be sensitive to visible and/or infra-red light, is provided for capturing images of a patient's pupils. If visible light is captured, the patient's eyelids can be open during the capturing, whereas if infra-red light is captured, the patient's eyelids can be closed during the capturing. The patient may be conscious or unconscious during the capturing. The camera 301 is coupled to a controller 302. The camera 301 may capture video data at any suitable sampling rate, for example in the range of approximately 1 Hz to approximately 1 kHz.

Typically, the controller 302 will comprise a microprocessor coupled to a memory. In some embodiments, a personal computer or other generic computing device may be used for the controller 302. The memory in the controller 302 stores instructions that, when executed by the microprocessor, cause the microprocessor to carry out operations for processing the captured video data from camera 302, processing it to determine a raw measure of pupil size, and determining from this one or more of: a depth of anesthesia for the patient, an index of cognitive activity for the patient, and a degree of perfusion of an anesthetic being administered to the patient to one or both hemispheres of the patient's brain. These operations are described in detail below with reference to FIG. 4. The controller 302 is coupled to an anesthesia machine 302 and a monitor 304. Thus, based on the results of the above operations, the controller 302 may control the operation of an anesthesia machine 303, for example to administer a dose of anesthetic or pain-relief medication, or a monitor 304 to trigger an alert.

Figure 4:
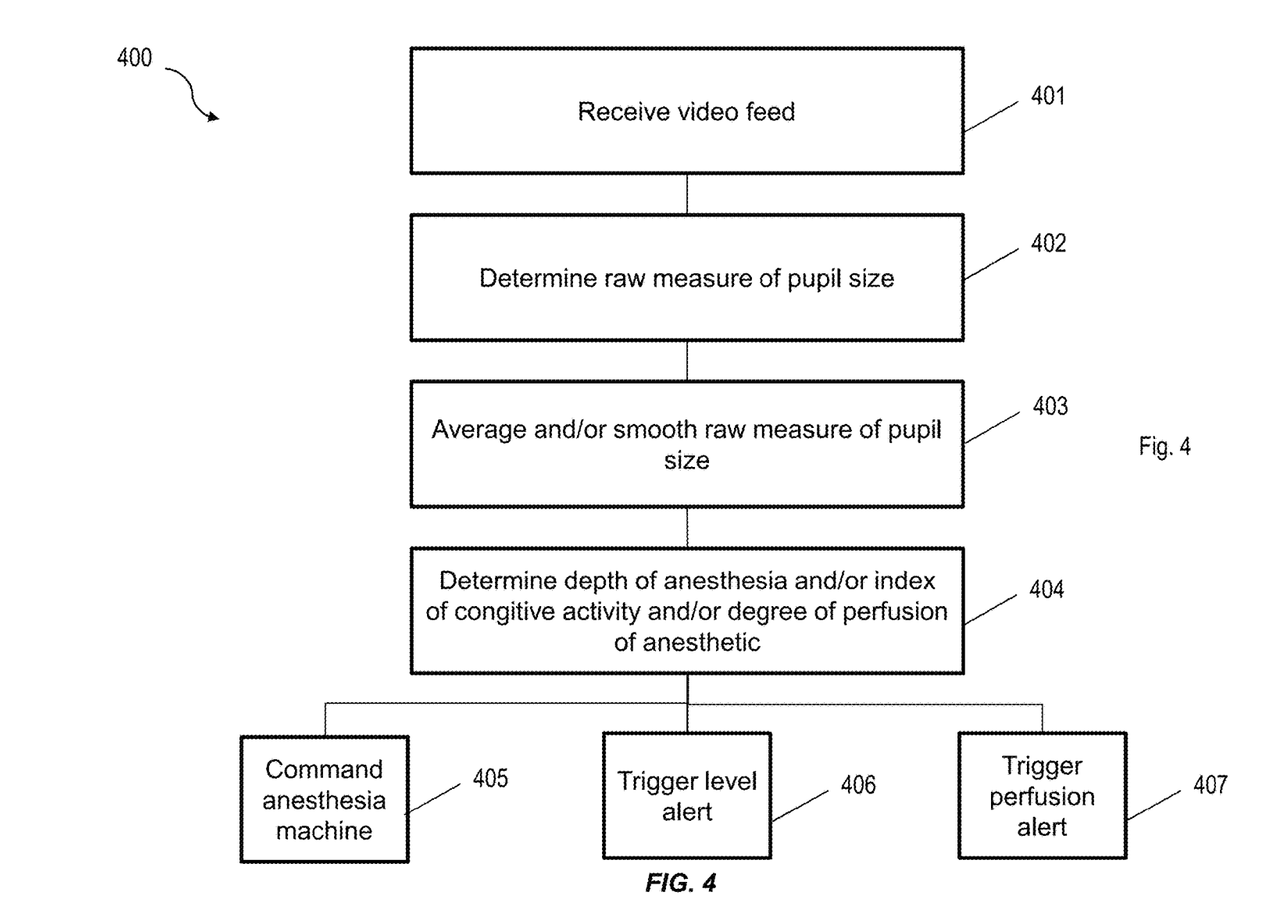
FIG. 4 shows a process flow diagram illustrating aspects of a method having one or more features consistent with implementations of the current subject matter.

FIG. 4 shows a process flow chart illustrating a method consistent with implementations of the current subject matter. The method illustrated in the flow chart can be performed by a system such as that depicted in FIG. 3 and described above. At 401, video image data is received, for example from a camera 301. Each frame of the video data includes image data representing either or both of a patient's pupils. This image data is processed at 402 to determine a raw measure of the pupil size of each pupil captured in the image data.

Any approach for determining the pupil size from the image data is within the scope of the current subject matter. One example of how this can be achieved is to identify the black (or near black) pixels in the image data, and walk the edge of those black pixels algorithmically to determine the outer diameter of what can be expected to be the pupil. The result can include the pupil diameter measured in pixels. This can further be converted to a standard unit of measurement, such as millimeters, by using an additional step such as a calibration procedure that determines the number of pixels to millimeters.

Optionally, at 403 the raw measure of pupil size determined at 402 may be averaged and/or smoothed to remove noise and/or data artifacts. Smoothing and averaging of the data may be performed in a variety of ways. For example, each data sample may be averaged with one or more preceding and subsequent data samples, and the data window can be altered (e.g., expanded or contracted) to encompass more or less preceding and subsequent data samples. Another example of smoothing or averaging can include using spline curves or sine waves to smooth the data. From the pupil size information resulted from 402 or optionally 403, one or more of the depth of anesthesia for a patient, an index of cognitive activity for a patient, and a degree of perfusion of an anesthetic being administered to a patient to one or both hemispheres of a brain of the patient is determined at 404.

Pupil size of one or both eyes can be used to determine the depth of anesthesia, where the larger the pupil, the greater the depth of anesthesia. The measurement of the pupil may be absolute, or relative to some pre-measured baseline pupil size (for example, when the patient was fully conscious). Differences in absolute (or relative) change in pupil size between left and right eyes may also indicate that anesthesia has not perfused evenly across both hemispheres of the brain. Uneven dilation between the pupils can be determined through the ongoing monitoring of pupil size of both eyes. The index of cognitive activity can be calculated by a series of processes, such as disclosed in U.S. Pat. No. 6,090,051.

Based on the results of the determining carried out at 404, the method may take one or more actions, which may be caused by the controller 302. For example, it may command at 405 an anesthesia machine 303 to change the amount of a drug, such as an anesthetic or pain-relief medication, being administered to a patient. Alternatively or in addition, it may trigger an alert at 406 if it is determined from 404 that a level of anesthesia for a patient is too high or too low. Another alert that may be triggered at 407 can indicate an anesthetic being administered is not perfusing correctly (for example, unequally or in inappropriate doses) to both hemispheres of the brain. The alerts triggered at 406 and/or 407 may be either visual alerts or audible alerts issued by a monitor 304.

Implementations of the current subject matter can include, but are not limited to, methods consistent with the descriptions provided herein as well as articles that comprise a tangibly embodied machine-readable medium operable to cause one or more machines (e.g., computers, etc.) to result in operations implementing one or more of the described features. Similarly, computer systems are also described that may include one or more processors and one or more memories coupled to the one or more processors. A memory, which can include a computer-readable storage medium, may include, encode, store, or the like one or more programs that cause one or more processors to perform one or more of the operations described herein. Computer implemented methods consistent with one or more implementations of the current subject matter can be implemented by one or more data processors residing in a single computing system or multiple computing systems. Such multiple computing systems can be connected and can exchange data and/or commands or other instructions or the like via one or more connections, including but not limited to a connection over a network (e.g. the Internet, a wireless wide area network, a local area network, a wide area network, a wired network, or the like), via a direct connection between one or more of the multiple computing systems, etc.

One or more aspects or features of the subject matter described herein can be realized in digital electronic circuitry, integrated circuitry, specially designed application specific integrated circuits (ASICs), field programmable gate arrays (FPGAs) computer hardware, firmware, software, and/or combinations thereof. These various aspects or features can include implementation in one or more computer programs that are executable and/or interpretable on a programmable system including at least one programmable processor, which can be special or general purpose, coupled to receive data and instructions from, and to transmit data and instructions to, a storage system, at least one input device, and at least one output device. The programmable system or computing system may include clients and servers. A client and server are generally remote from each other and typically interact through a communication network. The relationship of client and server arises by virtue of computer programs running on the respective computers and having a client-server relationship to each other.

These computer programs, which can also be referred to programs, software, software applications, applications, components, or code, include machine instructions for a programmable processor, and can be implemented in a high-level procedural language, an object-oriented programming language, a functional programming language, a logical programming language, and/or in assembly/machine language. As used herein, the term "machine-readable medium" refers to any computer program product, apparatus and/or device, such as for example magnetic discs, optical disks, memory, and Programmable Logic Devices (PLDs), used to provide machine instructions and/or data to a programmable processor, including a machine-readable medium that receives machine instructions as a machine-readable signal. The term "machine-readable signal" refers to any signal used to provide machine instructions and/or data to a programmable processor. The machine-readable medium can store such machine instructions non-transitorily, such as for example as would a non-transient solid-state memory or a magnetic hard drive or any equivalent storage medium. The machine-readable medium can alternatively or additionally store such machine instructions in a transient manner, such as for example as would a processor cache or other random access memory associated with one or more physical processor cores.

To provide for interaction with a user, one or more aspects or features of the subject matter described herein can be implemented on a computer having a display device, such as for example a cathode ray tube (CRT) or a liquid crystal display (LCD) or a light emitting diode (LED) monitor for displaying information to the user and a keyboard and a pointing device, such as for example a mouse or a trackball, by which the user may provide input to the computer. Other kinds of devices can be used to provide for interaction with a user as well. For example, feedback provided to the user can be any form of sensory feedback, such as for example visual feedback, auditory feedback, or tactile feedback; and input from the user may be received in any form, including, but not limited to, acoustic, speech, or tactile input. Other possible input devices include, but are not limited to, touch screens or other touch-sensitive devices such as single or multi-point resistive or capacitive trackpads, voice recognition hardware and software, optical scanners, optical pointers, digital image capture devices and associated interpretation software, and the like.

In the descriptions above and in the claims, phrases such as "at least one of" or "one or more of" may occur followed by a conjunctive list of elements or features. The term "and/or" may also occur in a list of two or more elements or features. Unless otherwise implicitly or explicitly contradicted by the context in which it used, such a phrase is intended to mean any of the listed elements or features individually or any of the recited elements or features in combination with any of the other recited elements or features. For example, the phrases "at least one of A and B;" "one or more of A and B;" and "A and/or B" are each intended to mean "A alone, B alone, or A and B together." A similar interpretation is also intended for lists including three or more items. For example, the phrases "at least one of A, B, and C;" "one or more of A, B, and C;" and "A, B, and/or C" are each intended to mean "A alone, B alone, C alone, A and B together, A and C together, B and C together, or A and B and C together." Use of the term "based on," above and in the claims is intended to mean, "based at least in part on," such that an unrecited feature or element is also permissible.

The subject matter described herein can be embodied in systems, apparatus, methods, and/or articles depending on the desired configuration. The implementations set forth in the foregoing description do not represent all implementations consistent with the subject matter described herein. Instead, they are merely some examples consistent with aspects related to the described subject matter. Although a few variations have been described in detail above, other modifications or additions are possible. In particular, further features and/or variations can be provided in addition to those set forth herein. For example, the implementations described above can be directed to various combinations and subcombinations of the disclosed features and/or combinations and subcombinations of several further features disclosed above. In addition, the logic flows depicted in the accompanying figures and/or described herein do not necessarily require the particular order shown, or sequential order, to achieve desirable results. Other implementations may be within the scope of the following claims.

What is claimed is:

1. A computer program product comprising a machine-readable medium storing instructions that, when executed by at least one programmable processor, cause the at least one programmable processor to perform operations comprising the steps:
   (i) receiving at least one video feed of a first pupil and a second pupil of a patient from at least one video camera positioned to view the first pupil and the second pupil;
   (ii) processing the at least one video feed to determine a raw measure of the sizes of the first pupil and the second pupil over time;
   (iii) determining, based on the raw measures of the sizes of the first pupil and the second pupil over time, that an unequal amount of anesthetic is being administered to one hemisphere or both hemispheres of the brain of the patient; and
   (iv) executing one or more actions based on the determining in step (iii).

2. The computer program product of claim 1, wherein:
step (i) comprises receiving a first video feed of the first pupil and a second video feed of the second pupil from at least one video camera position to view the pupils; and
step (ii) comprises processing the first video feed and the second video feed to determine the raw measure of the sizes of the pupils over time.

3. The computer program product of claim 1, wherein:
step (i) comprises receiving a first video feed of the first pupil from a first video camera position to view the first pupil, and receiving a second video feed of the second pupil from a second video camera position to view the second pupil; and
step (ii) comprises processing the first video feed and the second video feed to determine the raw measure of the sizes of the pupils over time.

4. The computer program method of claim 1, further comprising:
(a) receiving a video feed of a pupil of a patient from at least one video camera positioned to view the pupil; processing the video feed to determine a raw measure of the size of the pupil over time; determining, based at least in part on the raw measure of the pupil size over time, a depth of anesthesia for the patient, and causing execution of one or more actions based on the determining;
(b) receiving a video feed of a pupil of a patient from at least one video camera positioned to view the pupil; processing the video feed to determine a raw measure of the size of the pupil over time; determining, based at least in part on the raw measure of the pupil size over time, an index of cognitive activity for the patient, and causing execution of one or more actions based on the determining; or
(c) both (a) and (b).

5. The computer program product of claim 1, wherein the one or more actions comprise: commanding an anesthesia machine to change an administered amount of one or more drugs; triggering an alert indicating that a level of anesthesia for the patient is too high or too low; triggering an alert indicating that the anesthetic being administered to the patient has not perfused correctly to both hemispheres of the brain; or a combination of two or more of the foregoing.

6. The computer program product of claim 1, wherein the processing comprises sampling the video feed at approximately 1 Hz to 1000 Hz.

7. The computer program product of claim 1, wherein the operations further comprise at least one of averaging and smoothing the raw measure of pupil size to remove at least one of noise and data artifacts.

8. The computer program product of claim 1, wherein the at least one video camera comprises an infra-red light camera, and wherein the receiving comprises recording the video feed while an eyelid of the patient is closed.

9. The computer program product of claim 1, wherein the at least one video camera comprises a visible light camera, and wherein the receiving comprises recording the video feed while an eyelid of the patient is at least periodically opened.

10. The computer program product of claim 1, wherein the patient is receiving at least one of an anesthetic and a pain-relief medication during the receiving.

11. A system comprising computer hardware configured to perform operations comprising:
(i) receiving at least one video feed of a first pupil and a second pupil of a patient from at least one video camera positioned to view the first pupil and the second pupil;
(ii) processing the at least one video feed to determine a raw measure of the sizes of the first pupil and the second pupil over time;
(iii) determining, based on the raw measures of the sizes of the first pupil and the second pupil over time, that an unequal amount of anesthetic is being administered to one hemisphere or both hemispheres of the brain of the patient; and
(iv) executing one or more actions based on the determining in step (iii).

12. The system of claim 11, wherein:
step (i) comprises receiving a first video feed of the first pupil and a second video feed of the second pupil from at least one video camera position to view the pupils; and
step (ii) comprises processing the first video feed and the second video feed to determine the raw measure of the sizes of the pupils over time.

13. The system of claim 11, wherein:
step (i) comprises receiving a first video feed of the first pupil from a first video camera position to view the first pupil, and receiving a second video feed of the second pupil from a second video camera position to view the second pupil; and
step (ii) comprises processing the first video feed and the second video feed to determine the raw measure of the sizes of the pupils over time.

14. The system of claim 11, wherein the computer hardware is further configured to perform operations comprising:
(a) receiving a video feed of a pupil of a patient from at least one video camera positioned to view the pupil; processing the video feed to determine a raw measure of the size of the pupil over time; determining, based at least in part on the raw measure of the pupil size over time, a depth of anesthesia for the patient, and causing execution of one or more actions based on the determining;
(b) receiving a video feed of a pupil of a patient from at least one video camera positioned to view the pupil; processing the video feed to determine a raw measure of the size of the pupil over time; determining, based at least in part on the raw measure of the pupil size over time, an index of cognitive activity for the patient, and causing execution of one or more actions based on the determining; or
(c) both (a) and (b).

15. The system of claim 11, wherein the computer hardware comprises a programmable processor; and a machine-readable medium storing instructions that, when executed by the processor, cause the at least one programmable processor to perform at least some of the operations.

16. The system of claim 11, further comprising one or more video cameras in communication with the programmable processor.

17. The system of claim 11, further comprising an anesthesia machine which is controllable by the programmable processor.

18. A computer-implemented method comprising:
(i) receiving at least one video feed of a first pupil and a second pupil of a patient from at least one video camera positioned to view the first pupil and the second pupil;
(ii) processing the at least one video feed to determine a raw measure of the sizes of the first pupil and the second pupil over time;

(iii) determining, based on the raw measures of the sizes of the first pupil and the second pupil over time, that an unequal amount of anesthetic is being administered to one hemisphere or both hemispheres of the brain of the patient; and (iv) executing one or more actions based on the determining in step (iii).

19. The computer-implemented method of claim 17, wherein at least one of the receiving, the processing, the determining and the causing is performed by a system comprising computer hardware.

20. The computer-implemented method of claim 17, wherein:

step (i) comprises receiving a first video feed of the first pupil and a second video feed of the second pupil from at least one video camera position to view the pupils; and step (ii) comprises processing the first video feed and the second video feed to determine the raw measure of the sizes of the pupils over time.

21. The computer-implemented method of claim 17, wherein:

step (i) comprises receiving a first video feed of the first pupil from a first video camera position to view the first pupil, and receiving a second video feed of the second pupil from a second video camera position to view the second pupil; and step (ii) comprises processing the first video feed and the second video feed to determine the raw measure of the sizes of the pupils over time.

22. The computer-implemented method of claim 17, further comprising:

(a) receiving a video feed of a pupil of a patient from at least one video camera positioned to view the pupil; processing the video feed to determine a raw measure of the size of the pupil over time; determining, based at least in part on the raw measure of the pupil over time, a depth of anesthesia for the patient, and causing execution of one or more actions based on the determining;

(b) receiving a video feed of a pupil of a patient from at least one video camera positioned to view the pupil; processing the video feed to determine a raw measure of the size of the pupil over time; determining, based at least in part on the raw measure of the pupil size over time, an index of cognitive activity for the patient, and causing execution of one or more actions based on the determining; or (c) both (a) and (b).

\* \* \* \* \*